(12) United States Patent
Flores et al.

(10) Patent No.: US 12,181,457 B2
(45) Date of Patent: Dec. 31, 2024

(54) METHOD AND SYSTEM FOR AROMA MAPPING

(71) Applicant: International Business Machines Corporation, Armonk, NY (US)

(72) Inventors: Romelia H. Flores, Keller, TX (US); Susan Christian, Grapevine, TX (US); Juel Daniel Raju, Garland, TX (US); Christopher Bryan Barnwell, Grapevine, TX (US)

(73) Assignee: International Buisiness Machines Corporation, Armonk, NY (US)

( * ) Notice: Subject to any disclaimer, the term of this patent is extended or adjusted under 35 U.S.C. 154(b) by 485 days.

(21) Appl. No.: 17/483,874

(22) Filed: Sep. 24, 2021

(65) Prior Publication Data

US 2023/0102429 A1 Mar. 30, 2023

(51) Int. Cl.
*G01N 33/00* (2006.01)
*G01N 33/02* (2006.01)
(Continued)

(52) U.S. Cl.
CPC ..... *G01N 33/0031* (2013.01); *G01N 33/0075* (2013.01); *G01N 33/02* (2013.01); *H04W 4/33* (2018.02); *H04W 4/38* (2018.02)

(58) Field of Classification Search
CPC ............... G01N 33/02; G01N 33/0031; G01N 33/0075; H04W 4/33; H04W 4/38; H04W 4/02
See application file for complete search history.

(56) References Cited

U.S. PATENT DOCUMENTS 10,314,492 B2  6/2019  Connor
10,412,985 B2  9/2019  Byron
(Continued)

FOREIGN PATENT DOCUMENTS

CN  104007763 A  8/2014
CN  104106973 A  10/2014
(Continued)

OTHER PUBLICATIONS

"Cognitive System for food tracking/ health control through data coming from house ovens," An IP.com Prior Art Database Technical Disclosure, Authors et. al.: Disclosed Anonymously, IP.com No. IPCOM000249016D, IP.com Electronic Publication Date: Jan. 26, 2017, 3 pages.
(Continued)

*Primary Examiner* — Benjamin R Schmitt
(74) *Attorney, Agent, or Firm* — CHIP LAW GROUP

(57) ABSTRACT

A computer-implemented method for generating an aroma map is disclosed. The computer-implemented method includes learning one or more aromas associated with one or more items. The computer-implemented method further includes identifying a presence of an item within a venue based on comparing one or more aromas detected by one or more sensors located within the venue with one or more learned aromas associated with the item. The computer-implemented method further includes identifying a micro-location of the item based, at least in part, on a location of the one or more sensors which detected the aroma. The computer-implemented method further includes generating an aroma map geospatially indicating the micro-location of the item within the venue.

14 Claims, 5 Drawing Sheets

(51) Int. Cl.
*H04W 4/33* (2018.01)
*H04W 4/38* (2018.01)

(56) References Cited

U.S. PATENT DOCUMENTS

| | | | |
|---|---|---|---|
| 2006/0191319 A1 | 8/2006 | Kurup | |
| 2013/0199266 A1 | 8/2013 | Maranon | |
| 2014/0201182 A1 | 7/2014 | Amin | |
| 2014/0282645 A1 | 9/2014 | Hammond | |
| 2015/0095301 A1 | 4/2015 | Amin | |
| 2015/0149120 A1 | 5/2015 | Burkhardt | |
| 2016/0091419 A1 | 3/2016 | Watson | |
| 2016/0170996 A1 | 6/2016 | Frank | |
| 2017/0090070 A1* | 3/2017 | Root | G01W 1/08 |
| 2017/0369168 A1 | 12/2017 | Hwang | |
| 2018/0084809 A1 | 3/2018 | Byron | |
| 2019/0236678 A1* | 8/2019 | Wilkinson | G06Q 30/0631 |

FOREIGN PATENT DOCUMENTS

| | | |
|---|---|---|
| EP | 0789239 A1 | 8/1997 |
| EP | 3187852 A1 | 7/2017 |
| GB | 2379153 A | 3/2003 |
| JP | 6655597 B2 | 2/2020 |
| KR | 20160041707 A | 4/2016 |
| WO | 2017007259 A1 | 1/2017 |

OTHER PUBLICATIONS

IBM, "Publishing in Science: Predicting how molecules smell", IBM Research Blog, Feb. 19, 2017, 8 pages, <https://www.ibm.com/blogs/research/2017/02/publishing-in-science-predicting-how-molecules-smell/>.

Katayama, Akiko, "How Aroma Bit Can Help You Visualize Smell", Forbes, Apr. 23, 2019, 4 pages, <https://www.forbes.com/sites/akikokatayama/2019/04/23/what-if-you-can-visualize-smell-aroma-bit-does-it-for-you/#750362e11be0.

Mell et al., "The NIST Definition of Cloud Computing", Recommendations of the National Institute of Standards and Technology, NIST Special Publication 800-145, Sep. 2011, 7 pages.

Service, Robert F., "Artificial intelligence grows a nose", Feb. 19, 2017, 6 pages, <https://www.sciencemag.org/news/2017/02/artificial-intelligence-grows-nose>.

* cited by examiner

METHOD AND SYSTEM FOR AROMA MAPPING

BACKGROUND

The present invention relates generally to the field of detecting and identifying aromas, and more particularly to the field of mapping items associated with identified aromas to particular geographic locations.

Different types of food have different smells and aromas. Some types of food have a very distinct and strong smell, such as garlic. Due to this, certain sections of restaurants and grocery stores have distinct smells and aromas based on the food nearby.

IoT sensors are used to detect and measure various physical phenomena such as sight, hearing, touch, taste, and smell. Odor imaging sensors detect and measure the smell in an area. Odor imaging sensors have receptor membranes with unique absorption-desorption characteristics. When odor molecules hit the membrane, the sensor monitors the interactions between them in the form of different frequencies. The results are expressed as patterns where different shapes indicate the molecular makeup of a smell as well as the intensity of the smell.

SUMMARY

According to one embodiment of the present invention, a computer-implemented method for generating an aroma map is disclosed. The computer-implemented method includes learning one or more aromas associated with one or more items. The computer-implemented method further includes identifying a presence of an item within a venue based on comparing one or more aromas detected by one or more sensors located within the venue with one or more learned aromas associated with the item. The computer-implemented method further includes identifying a micro-location of the item based, at least in part, on a location of the one or more sensors which detected the aroma. The computer-implemented method further includes generating an aroma map geospatially indicating the micro-location of the item within the venue.

According to another embodiment of the present invention, a computer program product for generating an aroma map is disclosed. The computer program product includes one or more computer readable storage media and program instructions stored on the one or more computer readable storage media. The program instructions include instructions to learn one or more aromas associated with one or more items. The program instructions further include instructions to identify a presence of an item within a venue based on comparing one or more aromas detected by one or more sensors located within the venue with one or more learned aromas associated with the item. The program instructions further include instructions to identify a micro-location of the item based, at least in part, on a location of the one or more sensors which detected the aroma. The program instructions further include instructions to generate an aroma map geospatially indicating the micro-location of the item within the venue.

According to another embodiment of the present invention, a computer system for generating an aroma map. The computer system includes one or more computer processors, one or more computer readable storage media, and program instructions stored on the computer readable storage media for execution by at least one of the one or more computer processors. The program instructions include instructions to learn one or more aromas associated with one or more items. The program instructions further include instructions to identify a presence of an item within a venue based on comparing one or more aromas detected by one or more sensors located within the venue with one or more learned aromas associated with the item. The program instructions further include instructions to identify a micro-location of the item based, at least in part, on a location of the one or more sensors which detected the aroma. The program instructions further include instructions to generate an aroma map geospatially indicating the micro-location of the item within the venue.

BRIEF DESCRIPTION OF DRAWINGS

The drawings included in the present disclosure are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
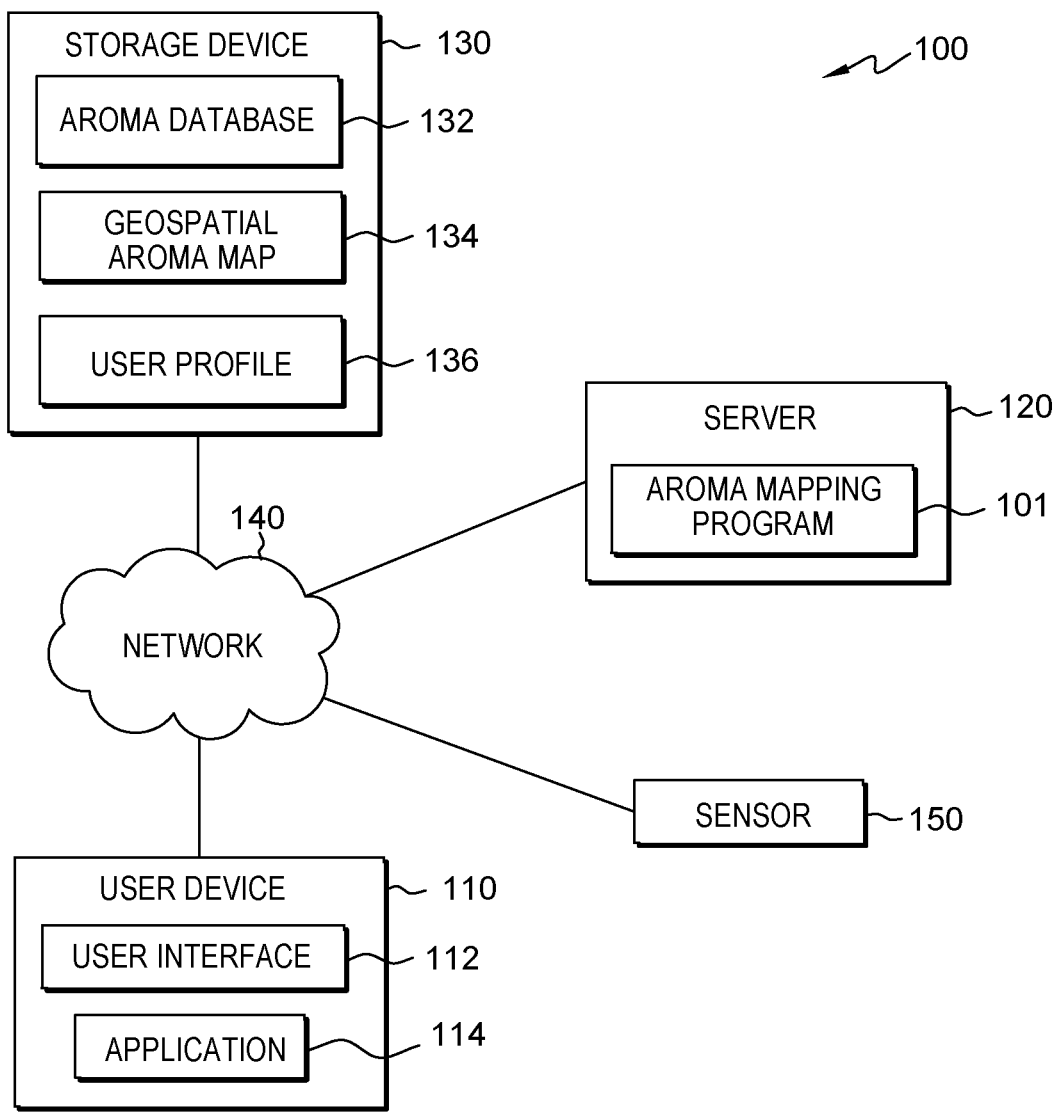
FIG. 1 is a block diagram of a network computing environment for generating an aroma map, generally designated 100, in accordance with at least one embodiment of the present invention.

While the embodiments described herein are amenable to various modifications and alternative forms, specifics thereof have been shown by way of example in the drawings and will be described in detail. It should be understood, however, that the particular embodiments described are not to be taken in a limiting sense. On the contrary, the intention is to cover all modifications, equivalents, and alternatives falling within the spirit and scope of the disclosure.

DETAILED DESCRIPTION

The present invention relates generally to the field of detecting and identifying aromas, and more particularly to the field of mapping items associated with identified aromas to particular geographic locations.

Restaurants, grocery stores, and markets offer a wide variety of foods. Different foods tend to have different smells and aromas associated with them. For example, a dish with garlic has a distinct and garlicy smell compared to a dish prepared with cinnamon. When in a setting with multiple dishes or food, it can be difficult for a person do discern what smell is associated with which dish or food. Oftentimes when in a restaurant, a person may smell something that smells pleasant to them and want to order the same dish. If a person knowns what dish or table the aroma the table is coming from, they can ask the waiter, waitress, or person at the table what the dish is. However, this can be very intrusive. With multiple other dishes being prepared and consumed around the person, it may be very difficult for the person to determine which dish is producing the desirable smell. It can be time consuming or inconclusive for a restaurant patron to inquire with a restaurant worker to determine what dish they believe is the dish creating such an aroma, which ultimately may leave the restaurant patron having to guess what menu item is generating the particular aroma.

Some people even wish to sit in certain areas of a restaurant based on the pleasant aromas of the seating area. Other people with allergies may need to sit away from certain areas of a restaurant based on aromas or nearby food they are allergic to. For example, if a person is extremely allergic to seafood, they may desire to be seated away from other tables who have ordered or are eating dishes with seafood.

Embodiments of the present invention recognize the need to identify the location of certain foods and aromas within a particular geographic area or venue. Embodiments of the present invention utilize aroma sensors to generate aroma maps. Embodiments of the present invention generates aroma maps which geospatially display the location or table where food is generating a certain aroma or smell. Embodiments of the present invention enable chefs or other restaurant/retail workers to train a system of the present invention to detect and identify particular aromas associated with particular items. Embodiments of the present invention further enable restaurant visitors, shoppers, hostesses, waitstaff, and other restaurant or store workers to locate items associated with particular aromas within a particular geographic area or venue on a visual map.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suit-able combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention will now be described in detail with reference to the Figures. FIG. 1 is a functional block diagram of a network computing environment for generating an aroma map to particular geographic locations, generally designated 100, in accordance with at least one embodiment of the present invention. In an embodiment, network computing environment 100 may be provided by cloud computing environment 50, as depicted and described with reference to FIG. 4, in accordance with at least one embodiment of the present invention. FIG. 1 provides an illustration of only one implementation and does not imply any limitations with regard to the environments in which different embodiments may be implemented. Many modifications to the depicted environment may be made by those skilled in the art without departing from the scope of the present invention as recited by the claims.

Network computing environment 100 includes user device 110, server 120, and storage device 130 interconnected over network 140. User device 110 may represent a computing device of a user, such as a laptop computer, a tablet computer, a netbook computer, a personal computer, a desktop computer, a personal digital assistant (PDA), a smart phone, a wearable device (e.g., smart glasses, smart watches, e-textiles, AR headsets, etc.), or any programmable computer systems known in the art. In general, user device 110 can represent any programmable electronic device or combination of programmable electronic devices capable of executing machine readable program instructions and communicating with server 120, storage device 130 and other devices (not depicted) via a network, such as network 140. User device 110 can include internal and external hardware components, as depicted and described in further detail with respect to FIG. 3.

User device 110 further includes user interface 112 and application 114. User interface 112 is a program that provides an interface between a user of an end user device, such as user device 110, and a plurality of applications that reside on the device (e.g., application 114). A user interface, such as user interface 112, refers to the information (such as graphic, text, and sound) that a program presents to a user, and the control sequences the user employs to control the program. A variety of types of user interfaces exist. In one embodiment, user interface 112 is a graphical user interface. A graphical user interface (GUI) is a type of user interface that allows users to interact with electronic devices, such as a computer keyboard and mouse, through graphical icons and visual indicators, such as secondary notation, as opposed to text-based interfaces, typed command labels, or text navigation. In computing, GUIs were introduced in reaction to the perceived steep learning curve of command-line interfaces which require commands to be typed on the keyboard. The actions in GUIs are often performed through direct manipulation of the graphical elements. In another embodiment, user interface 112 is a script or application programming interface (API).

Application 114 can be representative of one or more applications (e.g., an application suite) that operate on user device 110. In an embodiment, application 114 is representative of one or more applications (e.g., social media applications, web conferencing applications, and email applications) located on user device 110. In various example embodiments, application 114 can be an application that a user of user device 110 utilizes to view an aroma map that displays the particular ingredients associated with an item, the particular item associated with one or more detected aromas, and the location of an item associated with one or more detected aromas. In an embodiment, application 114 can be an application that a user of user device 110 utilizes to input information such as undesired aromas or items associated with undesired aromas (e.g., due to particular allergies) and desired aromas or items that an individual is interested in. Based on the particular aromas or items input by a user via application 114, an aroma map is generated that displays that particular location(s) of items associated with detected aromas and potential locations for a user to either avoid or gravitate towards. In an embodiment, application 114 can be a client-side application associated with a server-side application running on server 120 (e.g., a client-side application associated with aroma mapping program 101). In an embodiment, application 114 can operate to perform processing steps of aroma mapping program 101 (i.e., application 114 can be representative of aroma mapping program 101 operating on user device 110).

Server 120 is configured to provide resources to various computing devices, such as user device 110. In various embodiments, server 120 is a computing device that can be a standalone device, a management server, a web server, an application server, a mobile device, or any other electronic device or computing system capable of receiving, sending, and processing data, in an embodiment, server 120 represents a server computing system utilizing multiple computers as a server system, such as in a cloud computing environment. In an embodiment, server 120 represents a computing system utilizing clustered computers and components (e.g. database server computer, application server computer, web server computer, webmail server computer, media server computer, etc.) that act as a single pool of seamless resources when accessed within network computing environment 100. In general, server 120 represents any programmable electronic device or combination of programmable electronic devices capable of executing machine readable program instructions and communicating with each other, as well as with user device 110, storage device 130, sensor 150, and other computing devices (not shown) within network computing environment 100 via a network, such as network 140.

In an embodiment, server 120 includes aroma mapping program 101. In an embodiment, aroma mapping program 101 may be configured to access various data sources, such as aroma database 132, geospatial aroma map 134, and user profile 136 that may include personal data, content, contextual data, or information that a user does not want to be processed. Personal data includes personally identifying information or sensitive personal information as well as user information, such as location tracking or geolocation information. Processing refers to any operation, automated or unautomated, or set of operations such as collecting, recording, organizing, structuring, storing, adapting, altering, retrieving, consulting, using, disclosing by transmission, dissemination, or otherwise making available, combining, restricting, erasing, or destroying personal data. In an embodiment, aroma mapping program 101 enables the authorized and secure processing of personal data. In an embodiment, aroma mapping program 101 provides informed consent, with notice of the collection of personal data, allowing the user to opt in or opt out of processing personal data. Consent can take several forms. Opt-in consent can impose on the user to take an affirmative action before personal data is processed. Alternatively, opt-out consent can impose on the user to take an affirmative action to prevent the processing of personal data before personal data is processed. In an embodiment, aroma mapping program 101 provides information regarding personal data and the nature (e.g., type, scope, purpose, duration, etc.) of the processing. In an embodiment, aroma mapping program 101 provides a user with copies of stored personal data. In an embodiment, aroma mapping program 101 allows for the correction or completion of incorrect or incomplete personal data. In an embodiment, aroma mapping program 101 allows for the immediate deletion of personal data.

Figure 3:
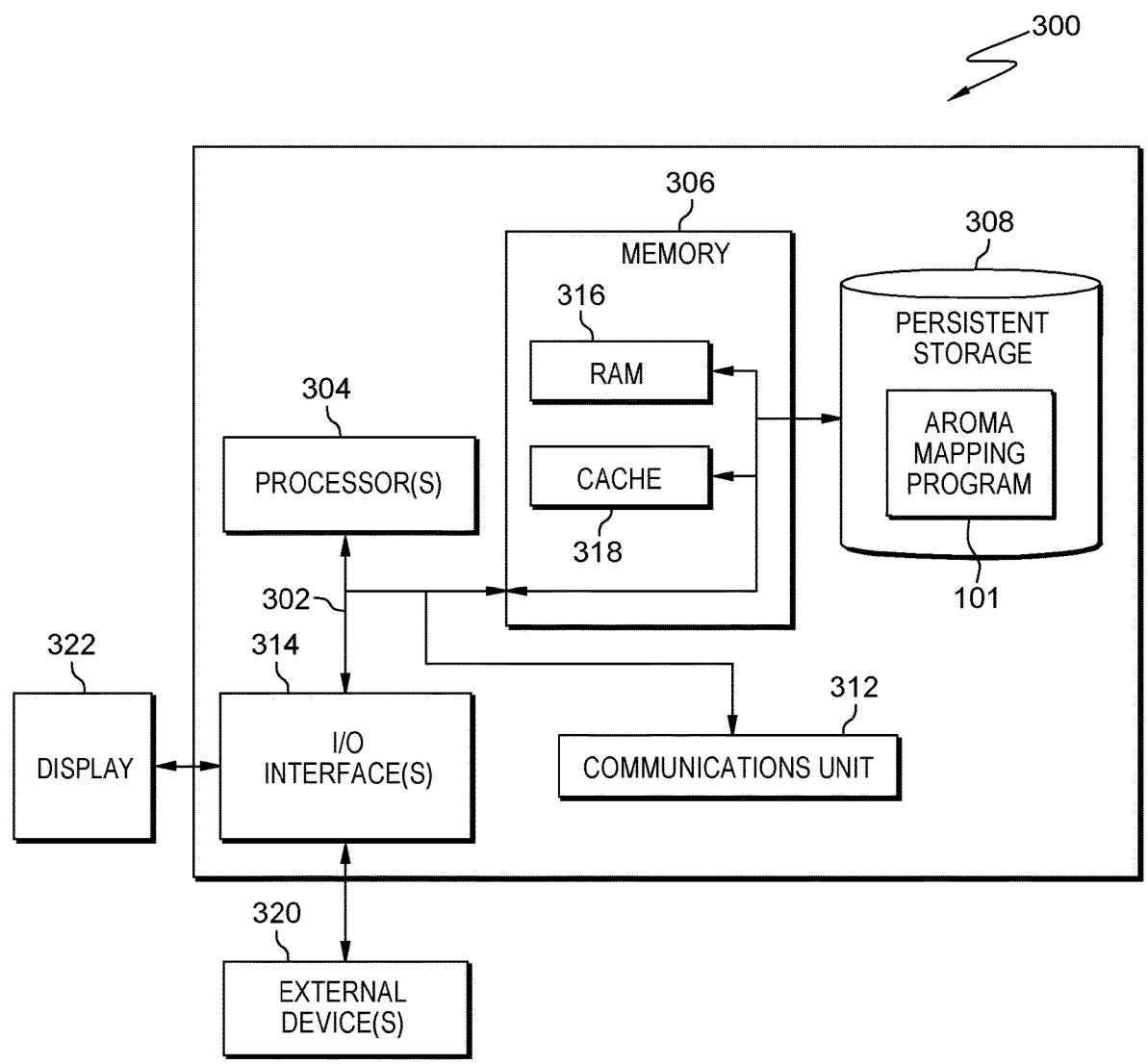
FIG. 3 is a block diagram depicting components of a computer, generally designated 300, suitable for executing an aroma mapping program 101 in accordance with at least one embodiment of the present invention.
Figure 4:
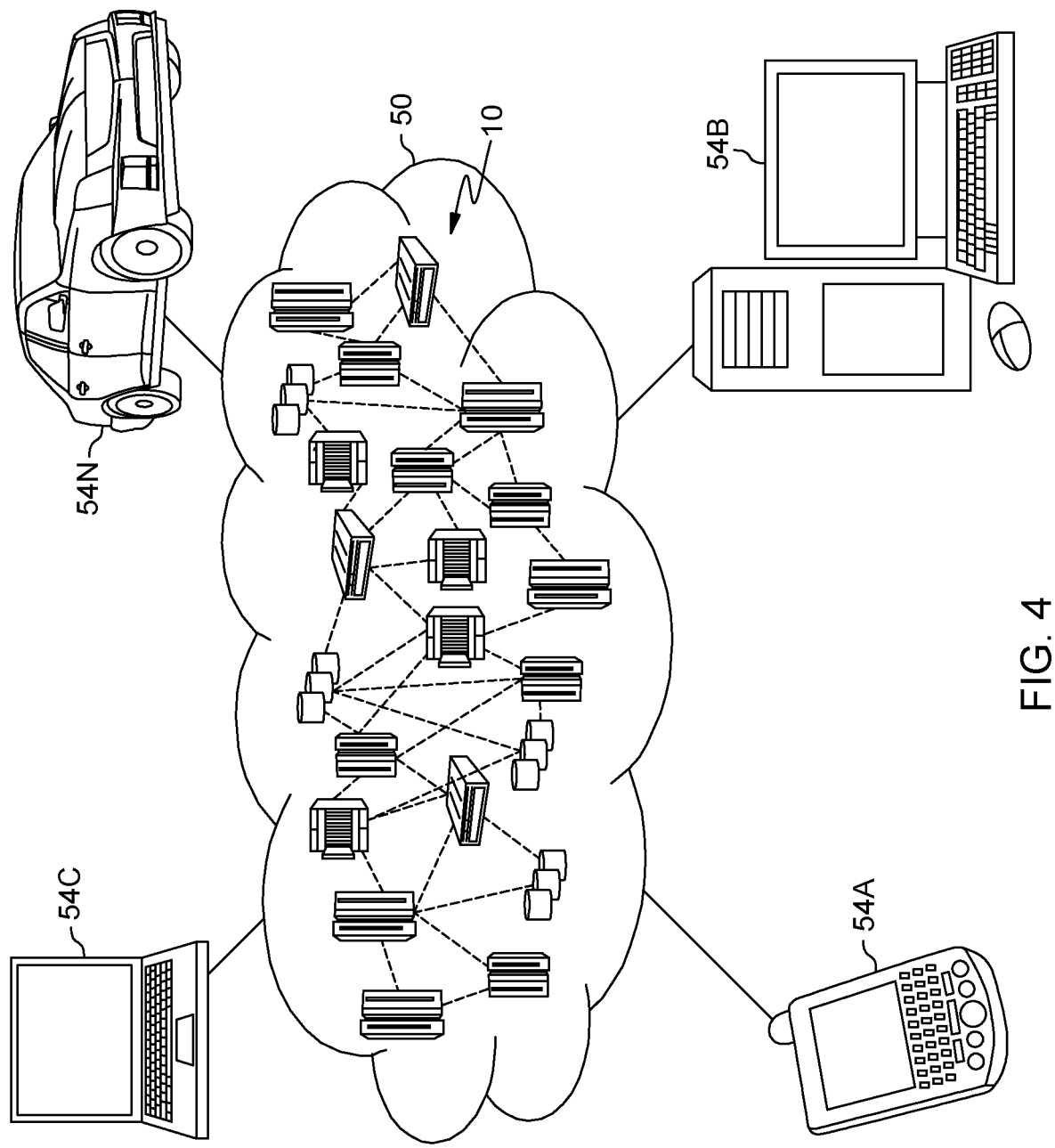
FIG. 4 is a block diagram depicting a cloud computing environment 50 in accordance with at least one embodiment of the present invention.

Server 120 may include components as depicted and described in detail with respect to cloud computing node 10, as described in reference to FIG. 4, in accordance with at least one embodiment of the present invention. Server 120 may include components, as depicted and described in detail with respect to computing device 300 of FIG. 3, in accordance with at least one embodiment of the present invention.

In various embodiments, storage device 130 is a secure data repository for persistently storing information on aroma maps, aroma sensor placement maps, and user profiles utilized by various applications and user devices of a user, such as user device 110. Storage device 130 may be implemented using any volatile or non-volatile storage media known in the art for storing data. For example, storage device 130 may be implemented with a tape library, optical library, one or more independent hard disk drives, multiple hard disk drives in a redundant array of independent disks (RAID), solid-state drives (SSD), random-access memory (RAM), and any possible combination thereof. Similarly, storage device 130 may be implemented with any suitable storage architecture known in the art, such as a relational database, an object-oriented database, or one or more tables.

In an embodiment, aroma database 132 contains information on the various aromas associated with one or more items, such as different types of food items located on a menu, and items located within a particular geographical location or venue. For example, aroma database 132 contains information on one or more aromas associated with the ingredients for the menu item "seafood pasta". In an embodiment, aroma database 132 contains pre-determined aromas associated with ingredients for one or more items. For example, a user can train, pre-load or otherwise indicate to aroma mapping program 101 the specific chemical makeup of aromas associated with different types of food or current menu items available for purchase. For example, a user can put a seafood pasta dish near sensor 150 and indicate to aroma mapping program 101 this aroma is associated with the seafood pasta dish on the menu. This information is stored and accessed by aroma mapping program 101 in aroma database 132.

Geospatial aroma map 134 contains information on the aroma map of the particular geographical locations of a store, restaurant, or any particular location of items associated with detected and identified aromas. In an embodiment, geospatial aroma map 134 contains information on the geospatial layout of a store or restaurant. For example, geospatial aroma map 134 contains information on the location of sensors, bars, tables, booths, aisles, kitchen, counters, and hostess stand. In an embodiment, geospatial aroma map 134 contains information of the particular items present or ordered at particular locations of a venue. For example, geospatial aroma map 134 contains one or more aroma maps depicting the location of respective tables in which patrons at a restaurant ordered various food dishes. In an embodiment, geospatial aroma map 134 contains a list of the ingredients included in the various items present or ordered at particular locations at a moment in time.

User profile 136 contains information on a user's aroma and ingredient preferences. In an embodiment, a user can be a restaurant patron, shopper, restaurant worker, chef, waitress, waiter, or hostess. In an embodiment, user profile 136 contains information on a user's allergies or food preferences. For example, user profile 136 may contain information that user A prefers to order shrimp scampi dishes with extra garlic. In another example, user profile 136 may contain information that user B is allergic to seafood and prefers to be seated in areas where there is no seafood. In yet another example, user profile 136 may contain information that user C enjoys the smell of lavender and prefers to be seated in areas having an aroma of lavender. In an embodiment, user profile 136 contains information on past items the user has ordered. For example, user profile 136 may contain information that user A has ordered the truffle garlic bread the last three times they visited the restaurant. In an embodiment, user profile 136 contains information on how the user typically prepares certain dishes.

Sensor 150 is a sensor that detects smells or aromas. In an embodiment, sensor 150 is an IoT sensor or odor imaging sensor that detects the smell, aroma, or order. In an embodiment, one or more sensors 150 are placed geospatially around a restaurant, store, or any physical space to detect various aromas at particular locations within a geographic area. In an embodiment, sensor 150 is a radio-frequency identification (RFID) tag which uses electromagnetic fields to automatically identify and track tags attached to objects. In an embodiment, sensor 150 is located in the restaurant or store and can be attached to a plate, table, food packaging, or other object. However, it should be appreciated that sensor 150 can be any type of olfactory sensor(s) known in the art capable of detecting aromas or odors. In an embodiment, sensor 150 is used to train aroma mapping program 101 to detect specific aromas with specific menu items, plates, dishes, or aromas.

In an embodiment, aroma mapping program 101 is calibrated or trained to learn the aromas associated with each menu item or food. In an embodiment, aroma mapping program 101 receives information of aromas associated with each menu item or food. For example, menu item "Crab Cakes" is placed near sensor 150 and aroma mapping program 101 determines the specific aroma pattern for "Crab Cakes" based on the detected odors. For example, aroma mapping program 101 receives information from user or a chef indicating that particular aroma is menu item "Crab Cakes." Later, when a similar aroma pattern is detected, aroma mapping program 101 determines menu item "Crab Cakes" is nearby. In an embodiment, aroma mapping program 101 receives information from user or chef indicating the table or area of the restaurant the menu item is made for. In the previous example, aroma mapping program 101 receives information from user or chef indicating table 7 ordered the Crab Cakes and verifies the detected Crab Cake aroma by sensors near table 7. In an embodiment, menu items are associated with a predetermined deviation from the originally detected aroma pattern due to the distance from the sensor and food preparation variations. For example, one or more detected odors are determined to be associated with a particular item if the chemical makeup of the odors are within an acceptable, predetermined threshold amount.

In an embodiment, one or more RFID tags are used to determine the location of a menu item. For example, if it is determined that RFID tag 5 near table 7 is on a plate of menu item "garlic knots," then aroma mapping program 101 determines there is a garlic aroma near table 7.

In an embodiment, aroma mapping program 101 determines the presence of an aroma based on one or more odors detected by sensor 150. In an embodiment, aroma mapping program 101 identifies the presence of an item based, at least in part, on comparing one or more detected odors to known items associated with the one or more detected odors. In an embodiment, aroma mapping program 101 identifies the presence of an item based, at least in part, on comparing the one or more detected odors to items associated with the one or more detected odors that are present on a menu. In an embodiment, aroma mapping program 101 identifies the presence of an item based, at least in part, on comparing the one or more detected odors to items associated one or more detected odors for those items recently purchased or ordered within a predetermined time period. In an embodiment, the aroma mapping program 101 is calibrated, pre-loaded, or trained with known aromas and the chemical makeup thereof. In an embodiment, aroma mapping program 101 is trained by receiving information that a specific aroma belongs to a specific menu item, food, or dish. For example, crab cakes are placed near a sensor and aroma mapping program 101 receives information indicative that the particular aroma detected from the sensor is crab cakes. In an embodiment, aroma mapping program 101 is calibrated or trained to provide the basis of orders placed and/or served, and maps the orders to specific locations within the venue or aromas from an area.

In an embodiment, aroma mapping program 101 identifies the presence of an item within a venue based on comparing one or more aromas detected by one or more sensors 150 with one or more known aromas associated with the item. In an embodiment, aroma mapping program 101 compares the known aromas with the aroma detected to determine the menu item. In an embodiment, aroma mapping program 101 determines a menu item based on one or more aroma categories. For example, if a garlic aroma is detected, aroma mapping program 101 determines the detected aroma must be from a garlic aroma category from the menu such as garlic knots, garlic pizza, or garlic bread. In an embodiment, aroma mapping program 101 verifies the aroma detected by cross checking the menu items ordered by location. For example, if a garlic aroma is detected from sensor A near tables 1, 2, and 3, aroma mapping program 101 determines tables 1 and 3 are empty and menu item "garlic knots" was placed at table 2.

In an embodiment, aroma mapping program 101 determines the location of an item within a geographic area associated with an identified aroma. In an embodiment, aroma mapping program 101 determines the location of the item based on the location of sensor 150 that detected the aroma. For example, aroma mapping program 101 determines the aroma was detected by sensor 3 located near table numbers 3, 4, and 5. Here, aroma mapping program 101 determines the aroma location is near table numbers 3, 4, and 5. In another example, aroma mapping program 101 determines the aroma was detected by a sensor on a plate on table 7. Here, aroma mapping program 101 determines the aroma location is near table 7.

In an embodiment, aroma mapping program 101 determines the location of menu items ordered throughout the restaurant. In an embodiment, aroma mapping program 101 determines the location of an item within a geographic area associated with an identified aroma based, at least in part, on correlating a location of a detected aroma and an order placed for an item associated with the detected aroma within a predetermined period of time. For example, aroma mapping program 101 determines the location of a detected aroma for seafood and correlates the location to an order placed for menu item "seafood pasta" at a nearby table 20 minutes ago. In an embodiment, aroma mapping program 101 displays tables with orders pending, orders placed, and food served. For example, aroma mapping program 101 displays table 1 placed an order for garlic bread, table 2 has been served cinnamon churros 3 minutes ago, and table 3 is pending to place an order.

In an embodiment, aroma mapping program 101 determines the location of an item within a geographic area associated with an identified aroma based, at least in part, on determining that an order for a particular item was placed, receiving an indication that the particular item has been delivered, and detecting one or more odors associated with the item within a predetermined time period of delivery of the item. For example, if garlic aroma is detected by a sensor near tables 3, 4, and 5, and it is determined the menu item garlic bread was ordered and delivered to table 4 five minutes ago, aroma mapping program 101 determines the garlic aroma detected is from the garlic bread at table 4.

In an embodiment, aroma mapping program 101 identifies sensor placement and table proximity to the sensor and correlates aromas as they move throughout areas of the venue. For example, a waiter walks a plate of garlic bread from the kitchen to table 6 and sensors on tables 1 through 5 detect the aroma while the plate of garlic bread moves throughout the venue.

In an embodiment, aroma mapping program 101 generates an aroma map indicating the micro-location within the venue of one or more aromas or menu items associated with one or more detected aromas. In an embodiment, a size of the micro-location of an item associated with one or more detected aromas is determined by an aroma strength score associated with a menu item. In an embodiment, the higher the aroma strength score associated with an item, the larger the micro-location of an item. Similarly, the lower the aroma strength score associated with an item, the smaller the micro-location of an item. For example, a menu item containing a high amount of garlic which typically has a strong and distinct aroma, such as garlic pizza, may have a larger micro-location than a menu item of bread, which typically has a low aroma. In an embodiment, aroma mapping program 101 generates an aroma map based on the location, menu items, and aromas detected. In an embodiment, aroma mapping program 101 further indicates the ingredients for food items on the aroma map associated with detected aromas. For example, if it is determined that the menu item seafood scampi is at table 5, aroma mapping program 101 displays and indicates an aroma of seafood scampi, or more particularly an aroma of shrimp and scallops near table 5, and indicates the ingredients for seafood scampi.

In an embodiment, aroma mapping program 101 has predetermined time thresholds on certain foods or aromas. For example, aroma mapping program 101 may have a predetermined time threshold of 20 minutes on the aroma of cinnamon. Meaning, the cinnamon aroma will appear on the aroma map for 20 minutes after the food is served or the aroma is detected. In an embodiment, aroma mapping program 101 determines if sensor 150 still detects the same aroma. In the previous example, aroma mapping program 101 determines if sensor 150 still detects a cinnamon aroma after 20 minutes. Further, aroma mapping program 101 continuously checks sensor 150 for the cinnamon aroma until the cinnamon aroma is no longer detected.

In an embodiment, aroma mapping program 101 is continuously trained to learn changes to altered recipes or dishes. For example, if a menu item is now prepared with more garlic, after feedback that most restaurant patrons ordered the menu item with extra garlic, aroma mapping program 101 learns the aroma of the new altered recipe of the menu item.

In an example, a chef prepares a dish, places the dish near sensor 150, and indicates to aroma mapping program 101 that the aroma associated with this dish is truffle garlic bread. Aroma mapping program 101 receives information that table 7 ordered truffle garlic bread. Here, the truffle garlic bread is delivered to table 7 and aroma mapping program 101 indicates on the aroma map there is truffle garlic bread at table 7 with a truffle and garlic aroma nearby table 7.

In another example, a user who is a restaurant patron uses aroma mapping program 101 to determine nearby aromas they may smell. For example, restaurant patron may smell a pleasant cinnamon aroma near their table and uses aroma mapping program 101 to determine the table behind them has an order of apple pie causing the cinnamon smell.

In yet another example, a restaurant patron indicates they are allergic to or finds aromas of seafood unpleasant and wants to sit in a section of the restaurant where there is no to low seafood aroma. A waitress, hostess, or the restaurant patron utilizes aroma mapping program 101 to determine where in the restaurant there is a table where there is a no to low seafood aroma.

In an embodiment, aroma mapping program 101 receives user preferences or previous orders. For example, aroma mapping program 101 receives information that a user previously ordered the house soup with extra coriander. If the user orders the house soup again with extra coriander, it will have a different aroma than the regular house soup. If the user orders the house soup with extra coriander and a second user enjoys the aroma from the soup, aroma mapping program 101 indicates the aroma is the house soup with extra coriander.

In an embodiment, aroma mapping program 101 receives feedback from users. For example, aroma mapping program 101 receives feedback from a restaurant patron via application 114 that the restaurant patron enjoys their meal of fish tacos more when chef Joey prepares the dish. In an embodiment, aroma mapping program 101 collects and analyzes the feedback. For example, aroma mapping program 101 determines from the feedback that a majority of restaurant patrons like the fish tacos the best when prepared by chef Joey. In an embodiment, aroma mapping program 101 collects and shares the feedback to one or more other venue locations. In an embodiment, aroma mapping program 101 collects and shares recipes. For example, if it is determined that from the feedback that a majority of restaurant patrons like the fish tacos the best when prepared by chef Joey, aroma mapping program 101 collects the recipe chef Joey uses and shares the recipe with other restaurant locations.

In another example, aroma mapping program 101 receives feedback from restaurant patrons and determines 80% of restaurant patrons add spinach to their shrimp scampi. Here, aroma mapping program 101 displays data that the majority of restaurant patrons add spinach to their shrimp scampi.

Figure 2:
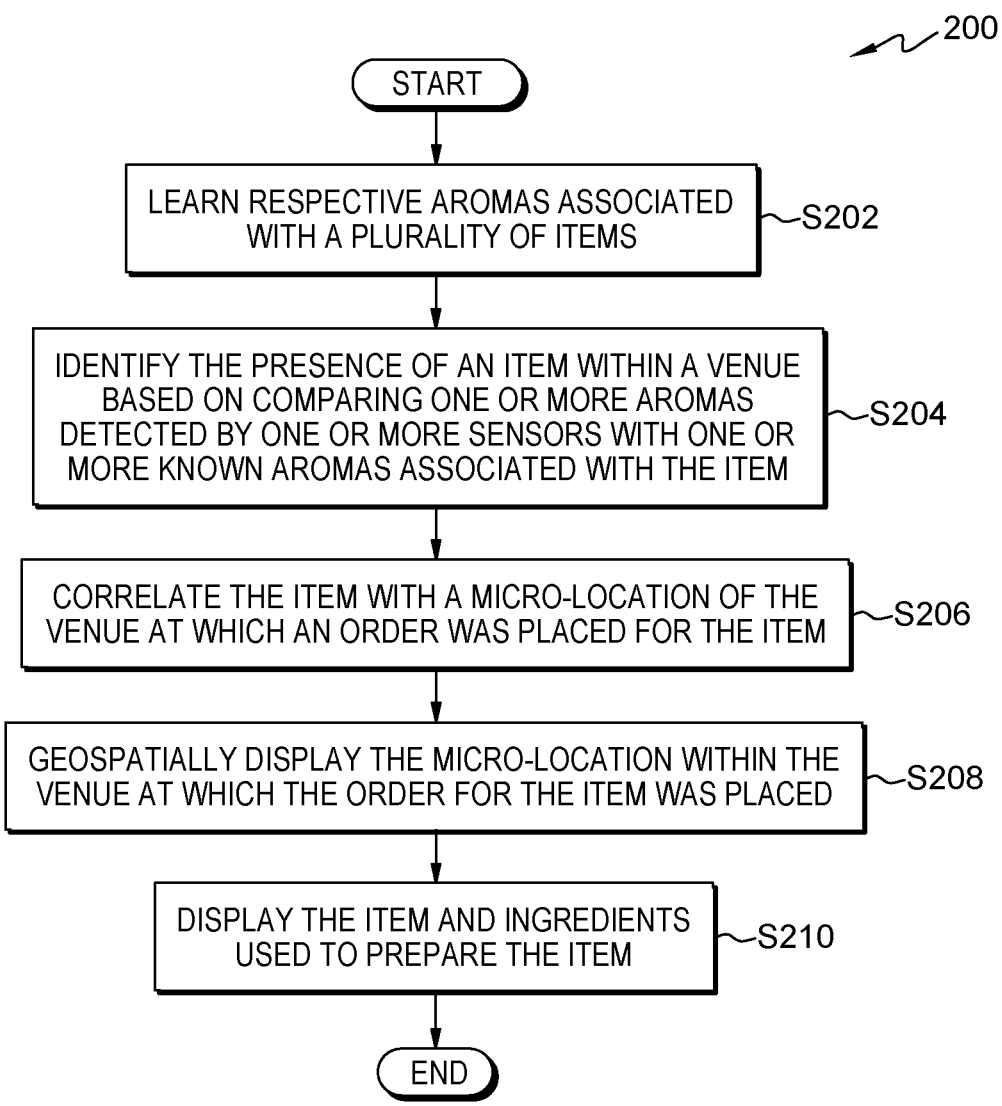
FIG. 2 is a flow chart diagram depicting operational steps for generating an aroma map, generally designated 200, in accordance with at least one embodiment of the present invention.

FIG. 2 is a flow chart diagram depicting operational steps for generating an aroma map, generally designated 200, in accordance with at least one embodiment of the present invention. FIG. 2 provides only an illustration of one implementation and does not imply any limitations with regard to the environments in which different embodiments may be implemented. Many modifications to the depicted environment may be made by those skilled in the art without departing from the scope of the invention as recited by the claims.

At step S202, aroma mapping program 101 learns respective aromas associated with a plurality of items. In an embodiment, aroma mapping program 101 is calibrated or trained to learn the aromas associated with each menu item or food. In an embodiment, aroma mapping program 101 learns a respective aroma by receiving information that a particular aroma is associated with a particular food item.

At step S204, aroma mapping program 101 identifies the presence of an item within a venue based on comparing one or more aromas detected by one or more sensors with one or more known aromas associated with the item.

At step S206, aroma mapping program 101 correlates the item with a micro-location of the venue at which an order was placed for the item. In an embodiment, aroma mapping program 101 determines the location of the item based on the location of the sensor that detected the aroma. In an embodiment, aroma mapping program 101 determines the location of the item based on the location of the table that ordered the particular item with the detected aroma.

At step S208, aroma mapping program 101 geospatially displays the micro-location within the venue at which the order for the item was placed.

At step S210, aroma mapping program 101 displays the item and ingredients used to prepare the item. In an embodiment, aroma mapping program 101 generates and displays an aroma map indicating the location of one or more aromas detected.

FIG. 3 is a block diagram depicting components of a computing device, generally designated 300, suitable for aroma mapping program 101 in accordance with at least one embodiment of the invention. Computing device 300 includes one or more processor(s) 304 (including one or more computer processors), communications fabric 302, memory 306 including, RAM 316 and cache 318, persistent storage 308, which further includes aroma mapping program 101, communications unit 312, I/O interface(s) 314, display 322, and external device(s) 320. It should be appreciated that FIG. 3 provides only an illustration of one embodiment and does not imply any limitations with regard to the environments in which different embodiments may be implemented. Many modifications to the depicted environment may be made.

As depicted, computing device 300 operates over communications fabric 302, which provides communications between computer processor(s) 304, memory 306, persistent storage 308, communications unit 312, and input/output (I/O) interface(s) 314. Communications fabric 302 can be implemented with any architecture suitable for passing data or control information between processor(s) 304 (e.g., microprocessors, communications processors, and network processors), memory 306, external device(s) 320, and any other hardware components within a system. For example, communications fabric 302 can be implemented with one or more buses.

Memory 306 and persistent storage 308 are computer readable storage media. In the depicted embodiment, memory 306 includes random-access memory (RAM) 316 and cache 318. In general, memory 306 can include any suitable volatile or non-volatile one or more computer readable storage media.

Program instructions for aroma mapping program 101 can be stored in persistent storage 308, or more generally, any computer readable storage media, for execution by one or more of the respective computer processor(s) 304 via one or more memories of memory 306. Persistent storage 308 can be a magnetic hard disk drive, a solid-state disk drive, a semiconductor storage device, read-only memory (ROM), electronically erasable programmable read-only memory (EEPROM), flash memory, or any other computer readable storage media that is capable of storing program instructions or digital information.

Media used by persistent storage 308 may also be removable. For example, a removable hard drive may be used for persistent storage 308. Other examples include optical and magnetic disks, thumb drives, and smart cards that are inserted into a drive for transfer onto another computer readable storage medium that is also part of persistent storage 308.

Communications unit 312, in these examples, provides for communications with other data processing systems or devices. In these examples, communications unit 312 can include one or more network interface cards. Communications unit 312 may provide communications through the use of either or both physical and wireless communications links. In the context of some embodiments of the present invention, the source of the various input data may be physically remote to computing device 300 such that the input data may be received, and the output similarly transmitted via communications unit 312.

I/O interface(s) 314 allows for input and output of data with other devices that may operate in conjunction with computing device 300. For example, I/O interface(s) 314 may provide a connection to external device(s) 320, which may be as a keyboard, keypad, a touch screen, or other suitable input devices. External device(s) 320 can also include portable computer readable storage media, for example thumb drives, portable optical or magnetic disks, and memory cards. Software and data used to practice embodiments of the present invention can be stored on such portable computer readable storage media and may be loaded onto persistent storage 308 via I/O interface(s) 314. I/O interface(s) 314 also can similarly connect to display 322. Display 322 provides a mechanism to display data to a user and may be, for example, a computer monitor.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider.

The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

FIG. 4 is a block diagram depicting a cloud computing environment 50 in accordance with at least one embodiment of the present invention. Cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
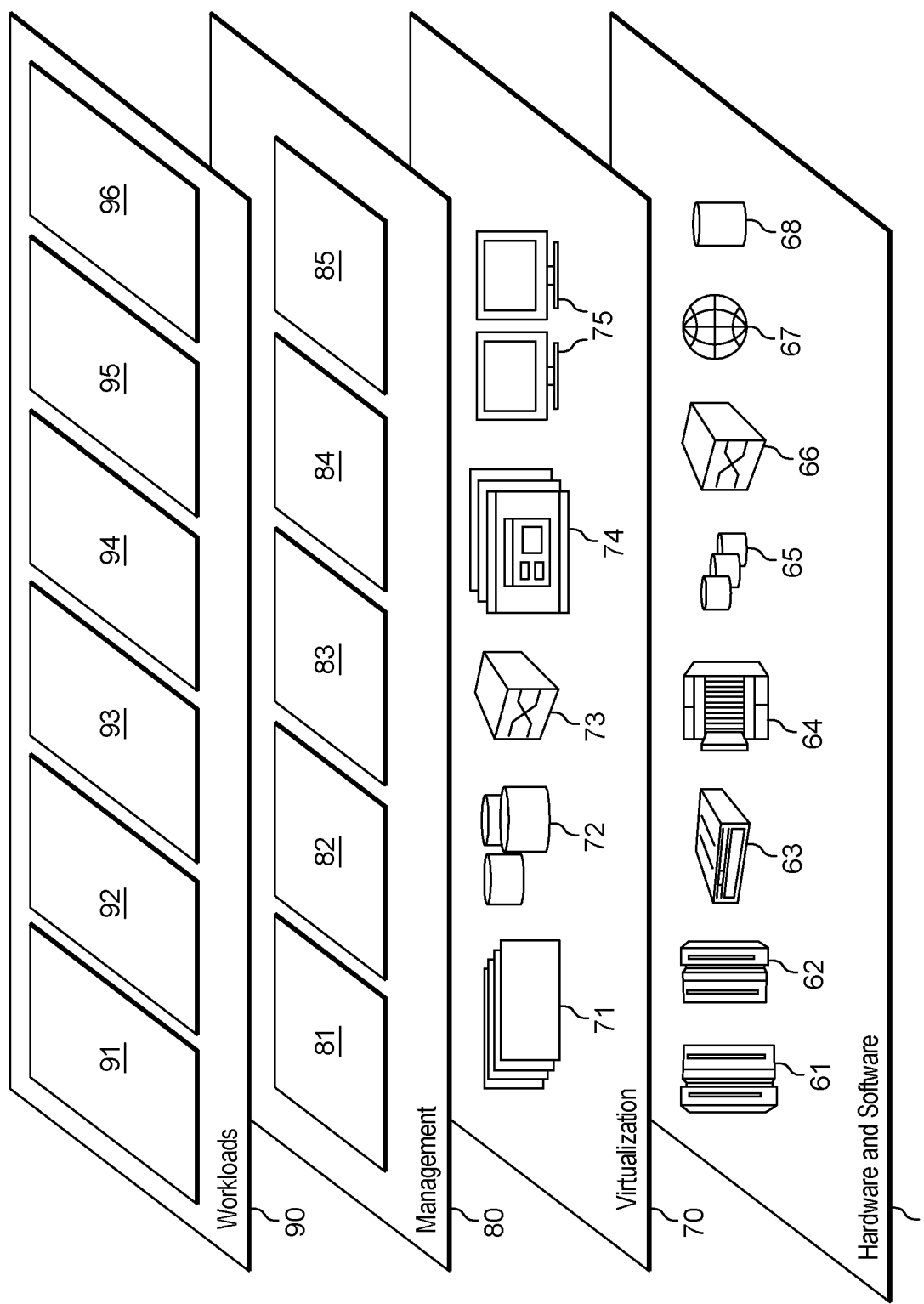
FIG. 5 is block diagram depicting a set of functional abstraction model layers provided by cloud computing environment 50 depicted in FIG. 4 in accordance with at least one embodiment of the present invention.

FIG. 5 is block diagram depicting a set of functional abstraction model layers provided by cloud computing environment 50 depicted in FIG. 4 in accordance with at least one embodiment of the present invention. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and aroma detection, identification, and mapping 96.

What is claimed is:

1. A computer-implemented method, comprising:
   learning one or more aromas associated with one or more items;
   identifying a presence of an item of the one or more items within a venue, based on comparing one or more aromas detected by one or more sensors located within the venue with the one or more learned aromas associated with the item;
   identifying a micro-location of the item based, at least in part, on:
      a location of the one or more sensors which detected the aroma, and
      the identifying of the presence of the item being within at least one of a determined time period of an order for the item being placed or a determined time period of the order for the item being completed; and
   generating an aroma map geospatially indicating the micro-location of the item within the venue.

2. The computer-implemented method of claim 1, wherein the identifying of the micro-location of the item is further based, at least in part, on detecting the one or more aromas associated with the item within the determined time period at a location within the venue at which the order was placed for the item.

3. The computer-implemented method of claim 1, wherein the generating of the aroma map geospatially indicating the micro-location of the item further includes displaying one or more ingredients used to prepare the item.

4. The computer-implemented method of claim 1, wherein a size of the micro-location of the item associated with the one or more detected aromas is based, at least in part, on an aroma strength score associated with the item.

5. The computer-implemented method of claim 1, wherein the micro-location of the item associated with the one or more detected aromas is based, at least in part on, a determined time threshold based on the detected aroma.

6. A computer program product comprising one or more computer readable storage media and program instructions stored on the one or more computer readable storage media for execution by one or more computer processors, the program instructions including instructions to:
   learn one or more aromas associated with one or more items;
   identify a presence of an item of the one or more items within a venue, based on comparing one or more aromas detected by one or more sensors located within the venue with the one or more learned aromas associated with the item;
   identify a micro-location of the item based, at least in part, on:
      a location of the one or more sensors which detected the aroma, and
      the identification of the presence of the item being within at least one of a determined time period of an order for the item being placed or a determined time period of the order for the item being completed; and
   generate an aroma map geospatially indicating the micro-location of the item within the venue.

7. The computer program product of claim 6, wherein the instructions to identify the micro-location of the item is further based, at least in part, on detecting the one or more aromas associated with the item within the determined time period at a location within the venue at which the order was placed for the item.

8. The computer program product of claim 6, wherein the instructions to generate the aroma map geospatially indicating the micro-location of the item further includes displaying one or more ingredients used to prepare the item.

9. The computer program product of claim 6, wherein a size of the micro-location of the item associated with the one or more detected aromas is based, at least in part, on an aroma strength score associated with the item.

10. The computer program product of claim 6, wherein the micro-location of the item associated with the one or more detected aromas is based, at least in part on, determined time threshold based on the detected aroma.

11. A computer system, comprising:
   one or more computer processors;
   one or more computer readable storage media; and
   computer program instructions;
   the computer program instructions being stored on the one or more computer readable storage media for execution by the one or more computer processors; and
   the computer program instructions including instructions to:
      learn one or more aromas associated with one or more items;
      identify a presence of an item of the one or more items within a venue based on comparing one or more aromas detected by one or more sensors located within the venue with the one or more learned aromas associated with the item;
      identify a micro-location of the item based, at least in part, on:
         a location of the one or more sensors which detected the aroma, and
         the identification of the presence of the item being within at least one of a determined time period of an order for the item being placed or a determined time period of the order for the item being completed; and
      generate an aroma map geospatially indicating the micro-location of the item within the venue.

12. The computer system of claim 11, wherein the instructions to identify the micro-location of the item is further based, at least in part, on detecting the one or more aromas associated with the item within the determined time period at a location within the venue at which the order was placed for the item.

13. The computer system of claim 11, wherein the instructions to generate the aroma map geospatially indicating the micro-location of the item further includes displaying one or more ingredients used to prepare the item.

14. The computer system of claim 11, wherein a size of the micro-location of the item associated with the one or more detected aromas is based, at least in part, on an aroma strength score associated with the item.

* * * * *